United States Patent [19]

Bargigia et al.

[11] Patent Number: 5,082,981
[45] Date of Patent: * Jan. 21, 1992

[54] PROCESS FOR THE SYNTHESIS OF PERFLUOROALKANDIENES

[75] Inventors: Gianangelo Bargigia; Vito Tortelli, both of Milan; Claudio Tonelli, Concorezzo; Silvana Modena, Monza, all of Italy

[73] Assignee: Ausimont S.p.A., Milan, Italy

[*] Notice: The portion of the term of this patent subsequent to Mar. 3, 2004 has been disclaimed.

[21] Appl. No.: 607,771

[22] Filed: Oct. 29, 1990

Related U.S. Application Data

[63] Continuation of Ser. No. 449,317, Dec. 11, 1989, abandoned, which is a continuation of Ser. No. 124,044, Nov. 23, 1987, abandoned.

[30] Foreign Application Priority Data

Nov. 27, 1986 [IT] Italy .............................. 22467 A/86

[51] Int. Cl.$^5$ ..................... C07C 17/00; C07C 17/26
[52] U.S. Cl. .................................... 570/156; 570/158
[58] Field of Search ............................... 570/156, 158

[56] References Cited

U.S. PATENT DOCUMENTS 3,444,251  5/1969  Gardner .
4,654,448  3/1987  Bargigia et al. .

FOREIGN PATENT DOCUMENTS 2028328  3/1980  United Kingdom .

Primary Examiner—Howard T. Mars
Attorney, Agent, or Firm—Morgan & Finnegan

[57] ABSTRACT

Perfluorobutadiene and higher alkandienes, with terminal double bonds, are obtained from α,ω-dibromo, α,ω-bromo, iodo perfluoroalkanes by dehalofluorination carried out with the aid of an organometallic compounds, in the presence of aprotic solvent belonging to the class of hydrocarbons or polar aprotic solvent belonging to the class of ethers, with limited reaction times.

5 Claims, No Drawings

PROCESS FOR THE SYNTHESIS OF PERFLUOROALKANDIENES

This application is a Continuation of application Ser. No. 124,044, filed Nov. 23, 1987, abandoned.

DESCRIPTION OF THE INVENTION

The present invention relates to a process for the synthesis of perfluorobutadiene and higher perfluoroalkandienes with terminal double bonds, by dehalofluorinating the α,ω-dibromo or α,ω-bromo, iodo perfluoroalkanes, carried out in the presence of organometallic compounds.

The perfluorobutadiene is a chemically interesting compound, because it has been proposed at a termonomer, in small amount together with $CF_2=CH_2$ and $C_3F_6$ to produce fluoroelastomers vulcanizable with peroxides (Jap. Pat. Daikin 47.752 pb. 7.7.77).

It has also been suggested as a termonomer together with $C_2F_4$ and trifluoronitrosomethane to obtain another vulcanizable fluorinated elastomer (see German Patent No. 2,304,650 and J. Chem. Soc. Perkin I 1973, page 1111). In fact, perfluorobutadiene reacts polymerizing through the 1-2 position, thus leaving a double bond unaltered and available for cross-linking reactions.

Besides perfluorobutadiene polymer is used as binder in "fluoro-oxidizer" systems,(see U.S. Pat. No. 3,980,509) wherein the polymer acts both as binder and fuel, whereas a saline fluoride such as $NH_4BF_4$ acts as oxidizing agent (see J. Appl. Polymer Sc. 19(1975), 1359).

Another patent (U.S. Pat. No. 3,353,904) mentions perfluoropolyenes containing end double bonds, as water-repellent agents used for cotton.

Although perfluorobutadiene is considered a very useful compound, the development of products which can be obtained starting from this compound has been limited because a synthesis of the compound which could be obtained on industrial scale was not available.

The known processes for synthetizing perfluorobutadiene and higher perfluorodienes are briefly mentioned hereinafter.

In U.S. Pat. No. 3,046,304 the starting materials are ICl and $CClF=CF_2$. By reacting these compounds, $CClFI—CClF_2$ is obtained which then dimerizes in the presence of an equal volume of Hg thus giving, with a yield of 82%, $CClF_2—CFCl—CClF_2$ which consequently can be dechlorinated by means of powdered Zn in ethyl alcohol to give perfluorobutadiene with a 98% yield.

This synthesis has the drawback to be carried out with difficulty on industrial scale because a wide amount of Hg has to be used for the dimerization and the reaction mixture has to be strongly stirred therefore, serious problems arise as regard the pollution and the apparatus.

Furthermore, in the subsequent dechlorination phase there is the problem to disperse the Zn powder in the reaction liquid phase and this offers remarkable difficulties. Moreover, the first step of the process, that is the reaction between $CClF=CF_2$ and ICl requires very long reaction times (6 weeks) and yields are rather low (72.6%), see C. A. 74 (1971) 126.097 h.

Higher perfluorodienes, such as 1,5-perfluorohexadiene, are obtained starting from $CF_2Cl—CFClI$ above mentioned, by telomerization of $C_2F_4$ in the presence of γ rays and under high pressure, thus obtaining the $CF_2ClCFCl$ $(C_2F_4)_2I$ telomer which is then chlorinated with chlorine in the presence of U.V. rays and then dehalogenated in two steps. In the first step, in the presence of Zn powder mixed with acetic acid + acetic anhydride, a double bond is formed by dechlorination, whereas in the second step, in the presence of powdered Zn in diethyleneglycol, dechlorofluorination occurs and the second double bond is formed (see CA 74(1971) 126097 h).

This method is complicate because of many reaction steps and the total yield is very low: furthermore, the use of radiations in an industrial process is complicated and cannot be proposed.

Finally it is known (see C.A. 98, (1983) 126788 e) a method for the preparation of perfluorobutadiene starting from $BrClFC—CBrF_2$ which is added (by telomerization) to $ClCF=CF_2$ in the presence of U.V. rays thus obtaining $BrF_2C—CClF—CBrF_2$. Said reaction product is dehalogenated using powdered Zn and acetic acid + acetic anhydride. The method is not applicable to higher perfluoroalkandienes. Also for this process the difficulties for an industrial realization are remarkable because of the use of U.V. rays and powdered Zn. Furthermore, the synthesis of the brominated intermediate containing 4 C atoms occurs with low yields on the $CClF=CF_2$.

In a copending Italian patent application No. 20935/A85 in the name of the Applicant a method for the preparation of perfluoroalkandienes of the general formula (I), as hereinafter indicated was described, said process comprised the deiodofluorination of α,ω-diiodoperfluoroalkanes.

It has now been unexpectedly found that it is possible to use as starting products α,ω-dibromoperfluoroalkanes and α, ω-bromoiodoperfluoroalkanes which by subsequent dehalogenation give final products of formula (II).

Therefore, it is an object of the present invention a process for the preparation of perfluoroalkandienes of the general formula:

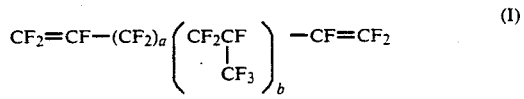

wherein a is an integer from 0 to 6, preferably from 0 to 4; b is an integer from 0 to 2 and the sum of a+b is comprised between 0 and 6, and the units having index a and b can be also alternated said process comprising dehalofluorinating of the α,ω-dibromo or α,ωbromo, iodeo indicated as diahalo hereinafter, perfluoroalkanes of the general formula:

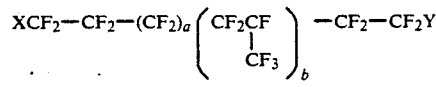

wherein X, Y=Br, I; X is different from Y in the case that X or Y=I.

with an organometallic compound, either in the presence of an aprotic solvent of the class of the hydrocarbons or in the presence of an aprotic polar solvent belonging to the class of ethers and cyclic ethers or mixtures thereof. As organometallic compound a halide of alkyl- or aryl-magnesium, dialkyl-magnesium or dialylmagnesium, Zn- and Cd-alkyls, an alkyl lithium or an aryl-lithium can be used. When perfluorohexadiene is prepared, it is preferable to use lithium -alkyl.

Generally, the organometallic compounds are used as solutions in ether solvents; when organometallic compounds of Li or Cd are used, the solutions of the sare in ether or hydrocarbon solvents are used.

Preferred solvents are dioxare, tetra-hydrofurare, diethylenglycoldimethylether, dimethoxyethare, hexane, octane, petroleum ether.

The reaction temperature is generally comprised between $-80°$ C. and $+150°$ C.

The reactants can be used in stoichiometric molar ratio or with a moderate excess or lack of the organometallic compound.

Starting dibromoperfluoroalkanes are known products, which can be obtained for instance directly as $\omega$-products together with the flame extinguishing $C_2F_4Br_2$ in the bromination reaction of $C_2F_5$ at high T or by telomerizing $C_2F_4$ or $C_2F_4/C_3F_6$ with $BrCF_2CFBr$ or of $C_3F_6Br_2$ with $C_2F_4$ or mixtures of perfluoroolefins. The same products are also obtained by reacting $Br_2$ with $C_2F_4$ and subsequent coupling or by telomerizing $C_2F_4$ with $CF_2Br_2$. By analogous and parallel action the $\alpha$, $\omega$-bromo, iodoperfluoroalkanes are obtained.

The dehalofluorination reaction must be carried out under specific working conditions in particular intended to avoid, if possible, the coexistence of the finished product and of the reagents and by products formed in the reaction medium. Besides keeping the reaction time if possible short, in the order of 30 minutes, or even less if the release of the reaction gaseous products can be controlled, it is also suitable to remove the finished product from the reaction medium, as soon as it is forming either by flowing as inert gas, or by distilling the reaction solvent at atmospheric pressure or at reduced pressure. In this last case the finished product is dragged away by the solvent during the distillation.

As above mentioned, in order to have a correct proceeding of the reaction, it is important that the reacting dihaloperfluoroalkane is dissolved in a suitable solvent selected among the ones previously mentioned.

In the practice it is suitable to mix the solution of the organometallic compound having a molar concentration from 0.2 to 2.5 and preferably from 0.5 to 1.5 molar in the above mentioned solvents, with a solution of the dihaloperfluoroalkane in a solvent of the same type or also in a different solvent which is inert towards the organometallic compound, for instance hexane.

EXAMPLES

The following examples are given to illustrate and not to limit the possible performances of the present invention.

EXAMPLE 1

9.0 g of $Br(C_2F_4)_2Br$ (0.025 mols) in 50 ml of tetrahydrofurane (THF) are introduced into a 150 ml round-bottomed flask provided with magnetic stirrer, dropping funnel, thermometer, reflux cooler joined with a trap at $-80°$ C.

The mixture is brought to boiling temperature and 50 ml of a 1M solution of $C_2H_5MgBr$ (0.05 moles) in tetrahydrofurane are introduced at such a velocity that the effervescence caused by the reaction can be controlled. The released gases are condensed in the trap at $-80°$ C.

2.8 g of a colorless liquid are collected which according to the gas-chromatographic analysis (G.C.) shows a single pick and according to the NMR analysis, IR analysis and boiling point it is identified as

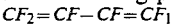

In the reactor 1.1 g of perfluorobutadiene remains together with the reaction solvent. Therefore, the yield is 96%.

EXAMPLE 2

10.8 g of $Br(C_2F_4)_2Br$ (0.03 moles) and 70 ml of anhydrous ethyl ether are introduced into a reactor equal to that of Example 1. After cooling to $-80°$ C. a solution of butyl-lithium in hexane (1.6M) (0.06 moles) is added, adjusting the addition rate so that the temperature of the reacting mass does not overcome $-70°$ C.

The mixture is allowed to spontareously heat to room temperature by flowing an inert gas, consequently it is brought to boiling temperature. A gareous product is released (identified as perfluorobutadiene) which is collected at $-80°$ C. in an amount equal to 4.6 g.

In addition to the solvent, the butyliodide corresponding to the used butillithium remains in the reactor.

The yield amounts to 94.7%.

EXAMPLE 3

8.1 g of $Br(C_2F_4)_2I$ (0.02 moles) in 40 ml of tetrahydrofurane hydrofurane (THF) are introduced into a 100 ml flask equipped with magnetic stirrer, dropping funnel, thermometer, reflux cooler joined with a trap at $-80°$ C.

The mixture is heated to boiling temperature and then 40 ml of a 1M solution of $C_2H_5MgBr$ (0.04 moles) in THF are introduced at such a velocity that the effervescence caused by the reaction can be controlled. The released gases are condensed in the trap at $-50°$ C. The product collected in the trap weighs 2.7 g and is identified as perfluorobutadiene. 0.3 g of perfluorobutadiene remain dissolved in the reaction solvent and the yield is therefore 92.6%.

EXAMPLE 4

Into a reactor analogous to the one of the preceding example, wherein however the cooler has been replaced by a Vigreux column, 9.6 g of $Br(C_2F_4)_3Br$ (0.02 moles) in 45 ml of anhydrous tetrahydrofurane are introduced. The mixture is heated to boiling temperature and 42 ml of a 1M solution of $C_2H_5MgBr$ (0.042 moles) in THF are introduced at such a rate to distill a sufficient amount of the debromofluorination product from the reaction mass.

The released gases are collected into a trap at $-80°$ C.

Thus 4.7 g of a liquid are separated said liquid at the gas-chromatographic examination shows the following picks:

a main pick corresponding to 71%; a shoulder corresponding to 25% and other lower peacks. The NMR. $^{19}F$ examination confirms that the main product is:

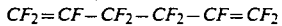

0.8 g of fluorinated products remain in the boiler; the products consist of n-perfluoro-1,5-hexadiene in an amount of 60%. The yield on hexadiene is 70%.

Comparison Example

Into the reactor of example 1, a sample of pure I(C$_2$F$_4$)$_2$I, weighing 11.3 g (0.025 moles) is introduced and heated to 50° C.; then the heat source is removed.

52 ml of C$_2$H$_5$MgBr 1.1M in THF are quickly dropped. Exothermy and effervescence are observed.

The product collected into the cooled trap, purified from traces of solvent, weighs 2 g and consists for 83% of perfluorobutadiene and for 17% of cyclobutadiene.

This last product is identified by NMR and gas-chromatography associated with the mass spectrophotometry; the perfluorobutadiene is identified by comparing its IR and NMR spectra with those known from the literature. In the reactor the perfluorobutadiene is no more present. The perfluorobutadiene yield is 41%.

What we claim is:

1. A process for preparing perfluoroalkandienes of formula:

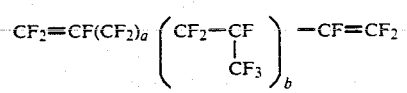

wherein a is an integer from 0 to 6, b is an integer from 0 to 2 and the sum a+b is between 0 and 6, comprising dehalo fluorinating α, ω-dibromo or α, ω-bromo, iodoperfluoroalkanes of the formula:

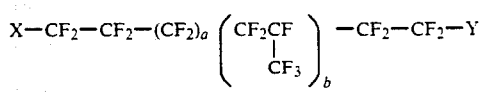

wherein X, Y=Br, I and X is different from Y if X or Y=I with an organometallic compound of Mg, Zn, Cd or Li, either in the presence of an aprotic solvent belionging to the hydrocarbon class or in the presence of an aprotic polar solvent belonging to the class of ethers and cyclic ethers and mixtures thereof, at temperature between −80° C. and +150° C.

2. The process according to claim 1, wherein the reaction product is removed from the reaction mixture whilte it is forming, by distilling it together with the reaction solvent or by flowing an inert gas.

3. The process according to claim 1, wherein the organometallic compound is selected among alkyl- or aryl magnesium, dialkylmagnesium, diarylmagnesium, Zn- or Cd-alkyl, lithium alkyl or lithium aryl.

4. The process according to claim 1, wherein perfluorohexadiene is obtained and as an organometallic compound lithium-alkyl is used.

5. The process for preparing perfluoroalkandienes according to claim 1 wherein the units (a) and (b) are alternated.

* * * * *